United States Patent [19]

Olsen et al.

[11] 4,452,894

[45] Jun. 5, 1984

[54] PSEUDOMONAS COMPOSITIONS

[75] Inventors: Ronald H. Olsen, Ann Arbor, Mich.; Peter A. Vandenbergh, Sarasota, Fla.

[73] Assignee: Microlife Genetics, Inc., Sarasota, Fla.

[21] Appl. No.: 310,090

[22] Filed: Oct. 9, 1981

[51] Int. Cl.$^3$ .................. C12N 1/20; C12N 15/00; C10G 32/00

[52] U.S. Cl. .................. 435/253; 435/172; 435/262; 435/281; 435/877; 435/875; 210/611; 210/909; 935/73; 935/59; 935/10

[58] Field of Search .............. 435/172, 253, 262, 281, 435/874, 875, 877; 210/611, 908, 909, 922

[56] References Cited

U.S. PATENT DOCUMENTS

| | | | |
|---|---|---|---|
| 3,808,101 | 4/1974 | Enei | 435/874 |
| 3,849,251 | 11/1974 | Nakayama | 195/29 |
| 3,923,603 | 12/1975 | Chakrabarty et al. | 435/874 |
| 4,259,444 | 3/1981 | Chakrabarty | 435/875 |

FOREIGN PATENT DOCUMENTS

0647339  2/1979  U.S.S.R. .................. 435/262

OTHER PUBLICATIONS

Gibson et al., "Oxidative Degradation of Aromatic Hydrocarbons by Microorganisms. II Metabolism of Halogenated Aromatic Hydrocarbons," Biochemistry, 7, (11), (11–1968), pp. 3795–3802.

Chatterjee et al., "Plasmids in the Biodegradation of Chlorinated Aromatic Compounds", Mol. Biol. Pathog. Ecol. Bact. Plasmids, (1981), pp. 519–528, Chem. Abst. 95:183636r.

Knackmuss et al., "Causes for the Retarded Microbial Total Degradation of Halogen-Substituted Hydrocarbons", Spez. Ber. Kernforschungsanlage Juelich, (1978), pp. 198–210, Chemical Abst. 92:72386c.

Yagi et al., "Degradation of Polychlorinated Biphenyls by Microorganisms", Journal WPCF, vol. 52, (5), (5–1980), pp. 1035–1043.

Van der Linden et al., "The Mechanisms of Microbial Oxidations of Petroleum Hydrocarbons", Advances in Enzymology, vol. 27, (1965), pp. 507–511.

Lichstein, H. C. and E. L. Oginsky, Experimental Microbial Physiology, W. H. Freeman and Company, San Francisco, Experiment 5, pp. 23–26, (1965).

Wigmore, G. J. and D. W. Ribbons, J. Bacteriol., 146, 920–927, Jun. 1981.

Reineke, W. and H. Knackmuss, Nature, 277:385, (1979).

Marinucci, A. C. and R. Bartha, Appl. Environ. Microbiol., 38:811–817, (1979).

Don, R. H. and J. M. Pemberton, J. Bacteriol., 145:681–686, (1980).

Hansen and Olsen, Journal of Bacteriology, 135:227–238, (1978).

Mercer and Loutit, J. of Bacteriology, 140:37–42, (1979).

Primary Examiner—Thomas G. Wiseman
Assistant Examiner—John Edward Tarcza
Attorney, Agent, or Firm—Ian C. McLeod

[57] ABSTRACT

Compositions of selected strains of Pseudomonas bacteria having the ability to utilize halogenated aromatic compounds as a sole carbon source are described. The bacteria are isolated from environments where they have been in long association with halogenated aromatic compounds, usually analagous compounds. First L-tryptophan and then a halogenated aromatic hydrocarbon are used as sole carbon sources for isolating and testing the selected strains. The isolated Pseudomonas strains are *Pseudomonas putida;* Pseudomonas sp. NRRL-B-12,538 or NRRL-B-12,539 or transfer derivatives thereof and are useful for degrading halogenated aromatic pollutants, particularly mono- and dichloroaromatics.

19 Claims, No Drawings

4,452,894

PSEUDOMONAS COMPOSITIONS

BACKGROUND OF THE INVENTION

1. Field of the Invention

The present invention relates to compositions including selected strains of Pseudomonas bacteria having the ability to degrade halogenated aromatic compounds. The invention particularly relates to strains of the species *Pseudomonas putida* wherein the ability to degrade the compounds is on a transferable plasmid.

2. Prior Art

L-tryptophan is an aromatic amino acid which is essential to the growth of certain microorganisms. It is synthesized by various strains of bacteria including strains of Pseudomonas as described in U.S. Pat. Nos. 3,808,101 and 3,849,251.

The prior art has described the use of the amino acid L-tryptophan as a sole carbon source for isolating strains of Pseudomonas from soils. This method is described by H. C. Lichstein and Evelyn L. Oginsky *Experimental Microbial Physiology*, W. H. Freeman and Company, San Francisco, Experiment 5, pages 23 to 26 (1965). The inventors have used this method for soil bacteria enrichment for many years. The bacteria produced by the method include mixed strains of Pseudomonas, wherein there is a potential for many different species and strains of Pseudomonas in the mixture. This prior art method is utilized in the present invention to isolate the selected strains of Pseudomonas.

The prior art has not thought that strains of Pseudomonas which utilize highly toxic halogenated toluenes or their analogs could be selected because the by-products (from the catabolic pathways) are toxic to the bacteria. This result can be seen from Wigmore, G. J. and Ribbons, D. W., J. Bacteriol., 146 920–927 (June 1981). Various publications have described strains of Pseudomonas which will grow on less toxic substrates but not the halogenated toluenes. These publications include Reineke, W., and H. Knackmuss, Nature, 277:385 (1979); Marinucci, A. C., and R. Bartha, Appl. Environ. Microbiol., 38:811–817 (1979) and Don, R. H., and J. M. Pemberton, J. Bacteriol., 145: 681–686 (1980). Some prior art bacteria are pathogenic.

OBJECTS

It is therefore an object of the present invention to provide compositions of selected strains of Pseudomonas which utilize L-tryptophan and a halogenated aromatic compound or mixtures thereof including particularly halogenated toluenes. Further it is an object of the present invention to provide Pseudomonas compositions which are non-pathogenic. These and other objects will become increasingly apparent from the following description.

GENERAL DESCRIPTION

The present invention relates to a bacterium of the genus Pseudomonas containing genetic material which controls utilization of a halogenated hydrocarbon as a sole carbon source, the genetic material being isolatable from a strain of *Pseudomonas putida* or *Pseudomonas* Sp. NRRL-B-12,538 or NRRL-B-12,539 in an environment with long association with a halogenated aromatic compound first by growth in a minimal medium including L-tryptophan as a sole carbon source and then growth in a second minimal medium in the presence of a halogenated aromatic compound as a second sole carbon source. A plasmid can be isolated in *Pseudomonas putida* which can be transferred to *Pseudomonas aeruginosa*.

The present invention particularly relates to a bacterium of the genus Pseudomonas having a genetic material from *Pseudomonas putida* isolated by the method of:

(a) providing a sample from an environment which contains halogenated aromatic compounds which have been in association with bacteria of the genus Pseudomonas for extended periods of time;

(b) isolating the Pseudomonas from the sample in a minimal medium containing L-tryptophan as the sole carbon source along with a nitrogen source and essential minerals;

(c) re-isolating the L-tryptophan isolated strains of the Pseudomonas in a confined space on a minimal medium containing as a sole carbon source a halogenated aromatic compound including the halogenated aromatic compound as a vapor; and (d) selecting for *Pseudomonas putida*.

SPECIFIC DESCRIPTION

The following Examples are illustrative of the preparation of the bacteria of the present invention.

EXAMPLE I

Four (4) soil samples were obtained from adjacent oil well pumping machinery which had been lubricated with high temperature halogenated aromatic oils and greases. The well was located in Mount Pleasant, Mich. and had been operating for many years.

A minimal medium was used as follows:

| | |
|---|---|
| Distilled water | 15 ml |
| Sodium and potassium phosphate buffer, 1 Molar | 0.6 ml |
| Essential Salt Mixture | 0.3 ml |
| Ammonium sulfate | 0.3 ml (0.3 ml of an 8% wt/vol Stock aqueous solution) |
| L-tryptophan | 4.0 ml (1% by wt aqueous solution) |
| Yeast Extract | 0.1 ml (10% by wt per volume) |

The medium uses the L-tryptophan as the sole carbon source. The yeast extract and ammonium sulfate provide nitrogen. The remainder of the medium provides any necessary inorganic salts and additional nitrogen.

The soil samples were each inoculated into the medium at the rate of 1 gram of soil to 20 ml of medium. The bacteria were grown in the minimal medium at 23° C. for 2 days four separate times followed by plating on a medium with the sole carbon source.

The isolates from the soil samples were grown on minimal medium agar plates in the presence of different chlorinated toluene position isomers in a closed container saturated with vapors of the isomer at ambient temperatures (23° C.). The m-, o- and p-chlorotoluene isomers were each provided in separate plates. It was found that one strain in particular (called OW III) grew well in the presence of all three isomers which was unexpected. Each of the isolated bacteria were replated on five agar plates and those isolates were retained as chlorinated toluene degrading bacteria. The isolates were designated as OW III, o-, m-, p-chlorotoluene or 2,6- or 3,4-dichlorotoluene, designating the isolating substrate for identification purposes.

The useful strains were deposited with Northern Regional Research Laboratory, Peoria, Illinois as *Pseudomonas putida* NRRL-B-12,537 and *Pseudomonas* sp. NRRL-B-12,538 and NRRL-B-12,539. The strains are shown in Table I. The strains did not have the ability to utilize toluene and p-toluic acid as can also be seen from Table I. Toluene and p-toluic acid are structural analogs of the chlorinated toluene derivatives. Normally soil isolates would be expected to grow on these analogs.

TABLE I

| Soil | Isolation Substrate | Toluene | p-toluic acid | o-Cl Tol | p-Cl Tol | m-Cl Tol |
|---|---|---|---|---|---|---|
| OW III NRRL-B-12,538 | o-Cl Tol | sl | sl | sl | +7 | — |
| OW III NRRL-B-12,537 | m-Cl Tol | sl | sl | +10 | +7 | +10 |
| OW III NRRL-B-12,539 | p-Cl Tol | sl | sl | sl | sl | +10 |

"sl" is slight growth and 10 is the best growth
"Tol" is Toluene

The isolate of Example I, OW III (m-chlorotoluene) was tested for temperature of growth. It was found to grow well at 25° C. and 30° C. The strains NRRL-B-12,538 and 12,539 were not characterized as to species. They had similar degradation characteristics to NRRL-B-12,537; however, they were not as effective in degrading halogenated aromatic compounds.

EXAMPLE II

In this example 2,6-dichlorotoluene and 3,4-dichlorotoluene utilization were tested. The OW III isolates of Example I were used. It was found that the isolates utilized these dichlorinated toluene position isomers. The best isolate, OW III (m-chlorotoluene), is apparent in Table II.

TABLE II

| Soil | Isolation Substrate | 2,6 di Cl Tol | 3,4 di Cl Tol |
|---|---|---|---|
| OW III | o-Cl Tol | +10 | +10 |
| OW III | m-Cl Tol | +10 | +10 |
| OW III | p-Cl Tol | sl | +10 |

EXAMPLE III

The isolates of Example I were used to degrade the monochlorinated toluenes, 2,6-dichlorotoluene; and 3,4-dichlorotoluene as carbon sources in the solid medium in the presence of toluene vapors. The results are shown in Table III.

TABLE III

| Soil | Isolation Substrate | Tol + o-Cl Tol | Tol + m-Cl Tol | Tol + p-Cl Tol | 3,4 di Cl Tol + Tol | 2,6 di Cl + Tol |
|---|---|---|---|---|---|---|
| OW III | o-Cl Tol | — | — | — | — | — |
| OW III | m-Cl Tol | +3 | +10 | +5 | — | +10 |
| OW III | p-Cl Tol | — | +10 | — | — | — |

The isolates were not able to utilize these chlorinated toluenes as effectively because toluene inhibited growth. This was an unexpected result and points out the uniqueness of these isolates i.e. growth on the halogenated compounds but not the parent compounds.

EXAMPLE IV

The bacterium (OW III mCl Tol) of Example I was treated to isolate and transform the plasmid.

Preparation of Plasmid DNA

Plasmid DNA was prepared by the method described by J. B. Hansen and R. H. Olsen, *J. Bacteriology* 135: 227–238 (1978).

Cells were grown overnight on the surface of TN-agar medium plates and were harvested from the surface of the plates by adding 10 ml sterile dilution water to each plate and scraping with a glass rod. This suspension was decanted into a bottle which was shaken vigorously to disperse clumps of cells.

All subsequent mixing was done by slow, gentle inversion. To lyse cells, we added lysozyme and ethylenediaminetetraacetate, and then sodium dodecyl sulphate (SDS) to 4% final concentration. Eight repeated cycles of heat pulse and mixing produced a clear, viscous lysate. DNA was denatured at pH 12.1–12.3 by adding 3 M NaOH and mixing for 3 min. at room temperature. Then tris (hydroxymethyl)aminomethane (pH 7.0) was added to return the pH below 9.0. We added SDS to 4% final concentration, NaCl to 1.0 M, and mixed by 20 inversions; after 6 hours at 4° C., the salt-precipitated chromosome-membrane complexes were pelleted by centrifugation at 17,000 g (4° C., 30 min.). The supernatant was mixed with polyethylene glycol 6000 to 10% concentration. After 6 hours at 4° C., the tubes were centrifuged at 700 g (4° C., 5 min.). Resuspension of the resulting pellets in 0.15 ml cold buffer gave plasmid-enriched DNA solution.

CsCl-ethidium bromide centrifugation was then done as described previously by Hansen and Olsen, *Journal of Bacteriology* 135: 227–238 (1978). DNA was stored frozen in TO buffer (Tris 10 mM-1 nM Na$_2$ EDTA, pH 8) and thawed slowly in ice water when used.

Transformation

Transformation experiments using *Pseudomonas aeruginosa* strain PAO 2178 (NRRL-B-12,535) as the recipient were conducted according to the method of Mercer and Loutit *J. of Bacteriology* 140:37–42 (1979). This recipient strain PAO 2178 is a derivative of PAO 1C which is unable to grow on any benzene related compounds because of the mutation in its catechol 1,2-oxygenase enzymatic activity. It contains no plasmids. This recipient was chosen because of the expectation that it would facilitate expression of the plasmid specified trait of chlorinated toluene degradation, unlike its parent which utilizes benzene related compounds. This surmise was proven to be true since it was possible to transfer this trait on the plasmid to PAO 2178 but not its parent PAO 1C. This appears to mean that the expression of the chlorinated toluene degradation gene trait on the plasmid requires a parent which does not have the same degradation characteristic on a chromosome which cancels the trait and makes it essentially non-functional on either the chromosome or the plasmid.

Bacteria were grown overnight on TN agar and a portion then inoculated into TN broth with incubation for 2 to 3 hours reaching a cell density of 1 × 10$^8$ per ml. The cells were centrifuged at 4° C. and the pellet suspended in one-half volume cold sterile MgCl$_2$ (0.15 M in distilled water). The pellet was dispersed and held in an ice-water bath for an additional 5 min. The cells were centrifuged and the pellet suspended as before but then held in the ice-water bath for 20 minutes. The cells were centrifuged again and the pellet suspended in one-tenth volume cold $MgCl_2$ (0.15 M).

Transforming-DNA (10 to 50 $\mu$l) was placed in a cold centrifuge tube and 0.2 ml of the above cells added with mixing. This mixture was incubated in an ice-water bath for 60 minutes followed by a heat-pulse in a water bath at 37° C. for 3 minutes while gently swirling the tube. The DNA-cell mixture was then placed immediately in an ice-water bath and incubated for 5 minutes. After this, 0.5 ml TN broth was added and the suspension incubated at 37° C. for 1 to 2.5 hours. The cells were then plated on selective medium and the plates were incubated at appropriate temperatures for 48 hours. With the acquisition of the plasmid, it was found that the PAO 2178 acquired the ability to utilize chlorinated hydrocarbons. The plasmid was reproduced by the bacterium deposited with NRRL as NRRL-B-12,536.

The foregoing Example IV illustrates the transformability of the *Pseudomonas putida* plasmids of the present invention into bacterial recipients which do not have the ability to utilize benzene related compounds. The plasmids can thus be transferred to numerous Pseudomonas strains which are or can be cured to be defective in the same respect for the transformation. In the transfer of the plasmid, it may fuse with genetic material in the recipient and thus not be identifiable as such. Obviously the transfer of the genetic material or plasmid can be of various other means including transduction and conjugal mating.

We claim:

1. A biologically pure culture of a bacterium of the genus Pseudomonas in a containing genetic material which promotes utilization of a wide variety of halogenated hydrocarbons as sole carbon sources and wherein the strain grows faster in the presence of o-, m- or p-chlorotoluene than toluene as a sole carbon source, the genetic material being isolatable from a strain of *Pseudomonas putida* or *Pseudomonas* sp. NRRL-B-12,538 or NRRL-B-12,539 in contact for extended periods of time with halogenated aromatic compounds first by growth in a minimal medium including L-tryptophan as a sole carbon source and then growth in a second minimal medium in the presence of a halogenated aromatic compound as a second sole carbon source and wherein growth of the bacterium is determined using a minimal medium agar plate in the presence of vapors of toluene or o-, m- or p-chlorotoluene as a sole carbon source at 25° to 30° C.

2. The bacterium of claim 1 wherein the genetic material is a plasmid in *Pseudomonas putida* NRRL-B-12,537.

3. The bacterium of claim 1 wherein the genetic material is in *Pseudomonas* sp. NRRL-B-12,538.

4. The bacterium of claim 1 wherein the genetic material is in *Pseudomonas* sp. NRRL-B-12,539.

5. The bacterium of claim 1 wherein the genetic material is in *Pseudomonas aeruginosa* NRRL-B-12,536.

6. A biologically pure culture of a bacterium of the genus Pseudomonas in a having genetic material from *Pseudomonas putida* isolated by the method of:

(a) providing a sample from an environment which contains halogenated aromatic compounds which have been in contact with bacteria of the genus Pseudomonas including *Pseudomonas putida* for extended periods of time;

(b) isolating the Pseudomonas from the sample in a minimal medium containing L-tryptophan as the sole carbon source along with a nitrogen source and essential minerals; and (c) re-isolating the L-tryptophan isolated strains of the Pseudomonas in the confined space on a minimal medium containing as a sole carbon source a halogenated aromatic compound wherein the bacterium grows faster in the presence of o, p, or m-chlorotoluene than toluene as a sole carbon source and wherein growth of the bacterium is determined using a minimal medium agar plate in the presence of vapors of toluene or o-, m- or p-chlorotoluene as a sole carbon source at 25° to 30° C.

7. The bacterium of claim 6 wherein the confined space in which the *Pseudomonas putida* is isolated is saturated with vapors of the halogenated aromatic compound.

8. The bacterium of claim 6 wherein in the preparation the environment is a soil containing halogenated aromatic compounds.

9. The bacterium of claim 6 wherein the environment from which the *Pseudomonas putida* is isolated is a halogenated hydrocarbon lubricant impregnated soil adjacent to operating oil pumping mchinery.

10. The bacterium of claim 6 wherein the halogenated aromatic compound is a m-, o- or p-chlorotoluene or dichlorotoluene.

11. The bacterium of claim 6 wherein the contains a plasmid which encodes for o, m or p-chlorotoluene utilization.

12. The bacterium of claim 11 wherein the Pseudomonas is *Pseudomonas putida*.

13. The bacterium of claim 6 wherein Pseudomonas is *Pseudomonas aeruginosa* containing a plasmid which encodes for o, m or p-chlorotoluene utilization transferred from the *Pseudomonas putida*.

14. The method of claim 13 wherein the transfer is by transformation.

15. A biologically pure culture of a bacterium of the genus Pseudomonas containing genetic material which encodes for halogenated aromatic compound degradation and in particular grows faster in the presence of o-, m- or p-chlorotoluene than toluene as a sole carbon source and which is derived from a Pseudomonas isolated from soil, wherein the isolated Pseudomonas has been in contact with a halogenated hydrocarbon lubricant in the soil for extended periods of time adjacent to an oil well and wherein growth of the bacterium is determined using a minimal medium agar plate in the presence of vapors of toluene or o-, m- or p-chlorotoluene as a sole carbon source at 25° to 30° C.

16. A biologically pure culture of a bacterium which is *Pseudomonas putida* NRRL-B-12,536.

17. A biologically pure culture of a bacterium which is *Pseudomonas* sp. NRRL-B-12,538.

18. A biologically pure culture of a bacterium which is *Pseudomonas* sp. NRRL-B-12,539.

19. A biologically pure culture of a bacterium which is *Pseudomonas aeruginosa* NRRL-B-12,536.

* * * * *

UNITED STATES PATENT AND TRADEMARK OFFICE
CERTIFICATE OF CORRECTION

PATENT NO. : 4,452,894
DATED : 1984 June 5
INVENTOR(S) : Ronald H. Olsen and Peter A. Vandenbergh It is certified that error appears in the above-identified patent and that said Letters Patent are hereby corrected as shown below:

Column 5, Claim 1, line 33 after "Pseudomonas" delete "in a".

Column 5, Claim 6, line 59 after "Pseudomonas" delete "in a".

Column 6, Claim 11, line 31, after "the" (second occurrence) insert --Pseudomonas--.

Signed and Sealed this

Nineteenth Day of March 1985

[SEAL]

Attest:

DONALD J. QUIGG

Attesting Officer

Acting Commissioner of Patents and Trademarks